(12) United States Patent
Hipsley (10) Patent No.: US 7,871,404 B2
(45) Date of Patent: Jan. 18, 2011

(54) SYSTEM AND METHOD FOR TREATING CONNECTIVE TISSUE

(76) Inventor: Annmarie Hipsley, 2976 Vincent Rd., Silver Lake, OH (US) 44224

( * ) Notice: Subject to any disclaimer, the term of this patent is extended or adjusted under 35 U.S.C. 154(b) by 1046 days.

(21) Appl. No.: 11/376,969

(22) Filed: Mar. 15, 2006

(65) Prior Publication Data

US 2007/0016175 A1    Jan. 18, 2007

Related U.S. Application Data

(60) Provisional application No. 60/662,026, filed on Mar. 15, 2005.

(51) Int. Cl.
*A61B 18/20* (2006.01)
(52) U.S. Cl. .................. 606/5; 606/4; 128/898
(58) Field of Classification Search ................ 606/2–9; 128/898
See application file for complete search history.

(56) References Cited

U.S. PATENT DOCUMENTS

| | | | |
|---|---|---|---|
| 5,354,331 A * | 10/1994 | Schachar | .............. 623/4.1 |
| 5,653,730 A | 8/1997 | Hammerslag | |
| 6,254,600 B1 * | 7/2001 | Willink et al. | ............... 606/41 |
| 6,263,879 B1 * | 7/2001 | Lin | ............... 128/898 |
| 2001/0016736 A1 * | 8/2001 | Lin | ............... 606/5 |
| 2001/0029363 A1 * | 10/2001 | Lin | ............... 606/5 |
| 2003/0028228 A1 | 2/2003 | Sand | |
| 2003/0059755 A1 | 3/2003 | D'Amico et al. | |
| 2003/0220630 A1 * | 11/2003 | Lin et al. | ............... 606/5 |
| 2005/0107774 A1 * | 5/2005 | Lin | ............... 606/4 |
| 2005/0205101 A1 * | 9/2005 | Lin | ............... 128/898 |
| 2005/0279369 A1 * | 12/2005 | Lin | ............... 128/898 |
| 2007/0225631 A1 * | 9/2007 | Bowlin et al. | ............... 602/52 |

\* cited by examiner

*Primary Examiner*—Henry M Johnson, III
*Assistant Examiner*—Jeffrey B Lipitz
(74) *Attorney, Agent, or Firm*—One LLP (57) ABSTRACT

A method and system of treating connective tissue to alter the biomechanical and fundamental properties of the connective tissue by forming perforations in the connective tissue to at least 90% of the depth or thickness of the connective tissue and maintaining the perforations in the connective tissue. The method alters the tissue to enhance the fundamental mechanisms involved in the immunology, biochemistry, and molecular genetics of the metabolism of the connective tissue. The connective tissue may be any desired connective tissue. The connective tissue of the eye may be removed to form a first desired pattern of perforations in the connective tissue of the eye at a first distance from the corneal center of the eye. Connective tissue is removed from the eye to form a second desired pattern of perforations in the tissue of the eye at a second distance from the corneal center of the eye.

15 Claims, 2 Drawing Sheets

SYSTEM AND METHOD FOR TREATING CONNECTIVE TISSUE

RELATED APPLICATION

The present application claims priority from U.S. Provisional Application No. 60/662,026, filed Mar. 15, 2005 herein incorporated by reference in its entirety.

TECHNICAL FIELD

The present invention relates to a system and method for treating connective tissue, and more specifically, to a system and method for treating connective tissue to alter the fundamental and biomechanical properties of the connective tissue.

BACKGROUND OF THE INVENTION

Connective tissue is tissue that supports and connects other tissues and parts of the body. The fundamental and biomechanical properties of connective tissue, such as scleral tissue of the eye, may change as it ages. These fundamental and biomechanical properties include, but are not limited to, the structure, function, immunology, elasticity, shock absorption, resilience, mechanical dampening, pliability, stiffness, rigidity, configuration, alignment, deformation, mobility, volume, biochemistry and molecular genetics of connective tissue proper and newly metabolized connective tissue. The alterations of these properties may result in an accumulation of low grade stress/strain of the connective tissue. This can occur by acute injury or as a normal gradual process of aging. The alterations of these properties of connective tissue may change the overall desired properties of the connective tissue and may also undesirably affect the surrounding tissues, structures, organs, or systems related to the connective tissue. Examples of such undesirable affects are increased tension, loss of flexibility, contracture, fibrosis, or sclerosis, which can prevent the connective tissue or structures that are related to the connective tissue from performing their desired function.

Alterations in fundamental and biomechanical properties, specifically its pliability and elasticity, of the scleral tissue of the eye may affect the ability of the eye to focus. These alterations of the scleral tissue may also contribute to an increase in the intraocular pressure and contribute to the loss of the contrast sensitivity of the eye or visual field of the eye. The biomechanical and structural alterations of the sclera may affect the refractive ability as well as the efficiency of the homeostatic functions of the eye such as intraocular pressure, aqueous production, pH balance, vascular dynamics, metabolism and eye organ function. Furthermore, these alterations of the scleral tissue may contribute to damage to the mechanoreceptors, photoreceptors, or sensory receptors in tissue layers and structures that are directly or indirectly related to the scleral tissue. Lastly, the fundamental and biomechanical alterations of the scleral tissue may also contribute to the ability of the cerebral cortex to process accurate visual stimulus necessary for processing visual signals into accurate visual perception.

It is known to ablate the surface of scleral tissue of an eye. The surface of the scleral tissue may be ablated to form radially extending incisions or excisions. It is also known to form spots along a ring on the surface of scleral tissue by ablation. A plurality of bands, inserts, or plugs may be inserted into the scleral tissue of an eye to expand the sclera.

SUMMARY OF THE INVENTION

The present invention relates to a method of altering the properties of connective tissue including forming and maintaining pores or perforations in the connective tissue to at least 90% of the depth or thickness of the connective tissue. The connective tissue may be any desired connective tissue, such as scleral tissue of the eye. The connective tissue of the eye may be removed to form a first desired pattern of perforations in the connective tissue of the eye at a first distance from the outer diameter of the posterior surgical limbus of the eye. The first desired pattern of perforations may have a plurality of perforations. Connective tissue is removed from the eye to form a second desired pattern of perforations in the tissue of the eye at a second distance from the outer diameter of the posterior surgical limbus of the eye. The second desired pattern of perforations may have a plurality of perforations.

The present invention also relates to a method of treating connective tissue. The method includes forming perforations in the connective tissue to at least 90% of the depth of the connective tissue. The method also includes at least partially affecting normal healing of the perforations.

The present invention also relates to a method of treating connective tissue to improve the biomechanics of the tissue. Such improvements include, but are not limited to, increase in elasticity, shock absorption, pliability, structural integrity and/or mobility. The method includes removing connective tissue of an eye to form a first desired pattern of perforations in the connective tissue of the eye at a first distance from the outer diameter of the posterior surgical limbus of the eye, the first desired pattern of perforations having a plurality of perforations. The method also includes removing tissue from the eye to form a second desired pattern of perforations in the tissue of the eye at a second distance from the outer diameter of the posterior surgical limbus of the eye, the second desired pattern of perforations having a plurality of perforations.

The present invention also relates to a system for treating connective tissue. The system include means for forming perforations in the connective tissue to at least 90% of the depth of the connective tissue. The system also includes means for at least partially affecting normal healing of the perforations.

The present invention further relates to a system for treating connective tissue to increase elasticity of the tissue comprising. The system includes means for removing connective tissue of an eye to form a first desired pattern of perforations in the connective tissue of the eye at a first distance from the outer diameter of the posterior surgical limbus of the eye, the first desired pattern of perforations having a plurality of perforations. The system also includes means for removing tissue from the eye to form a second desired pattern of perforations in the tissue of the eye at a second distance from the outer diameter of the posterior surgical limbus of the eye, the second desired pattern of perforations having a plurality of perforations.

BRIEF DESCRIPTION OF THE DRAWINGS

The foregoing and other features of the present invention will become apparent to one skilled in the art to which the present invention relates upon consideration of the following description of the invention with reference to the accompanying drawings, in which.

DESCRIPTION OF EMBODIMENTS

Figure 1:
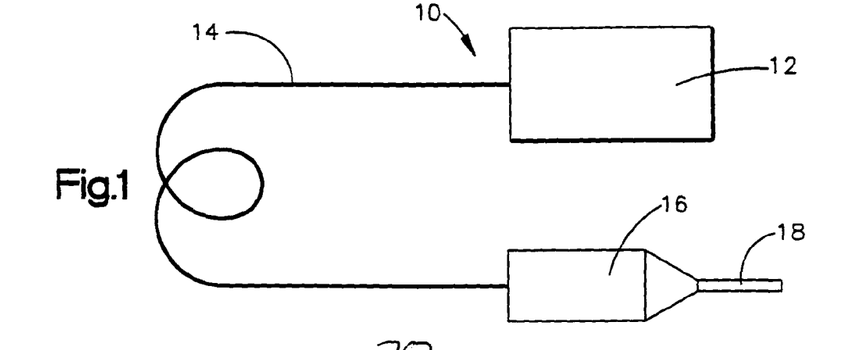
FIG. 1 is a schematic drawing of a system of the present invention for use in treating connective tissue.

A surgical laser system 10 for treating connective tissue is illustrated in FIG. 1. To treat the connective tissue, the system 10 accesses desired connective tissue. Access to the desired connective tissue can be done directly, such as by ablation. Also, access to the desired connective tissue can be done indirectly, such as by creating a flap, incision, excision, vaporization, or gap in overlying tissue or structure.

The surgical laser system 10 may be used to treat any desired connective tissue of the body. For example, in the eye, the surgical laser system may be used to treat the conjunctiva; the cornea (including all its layers and membranes); the iris; the ciliary body; the ciliary muscles; the anterior chamber; the zonula ciliaris; the subchoroidal lamina; the extraocular muscles and their associated connective tissues, membranes, and fascia; the posterior chamber; the lens and all of its associated layers, tissues, capsules, and membranes; the canal of schlemm and all of its associated layers, tissues, capsules, and membranes; the ora seratta; the vitreous body; the papilla nervi optici; the optic nerve; the lamina cribrosa; the choroid; the sclera; the retina; all epithelial cell layers in the eye; the vascular structures in the eye; the accessory organs of the eye; and the lymph vessels of the eye.

As another example, in the ear, the surgical laser system 10 may be used to treat the tympanic membrane, the crista ampullaris, the cochlear, the cochlear duct, and hair cells. As another example, the surgical laser system 10 may be used to treat tissue of the kidneys or tissue of the ovaries. As another example, the surgical laser system 10 may be used to treat large aponeuroses, such as lumbosacral fascia, abdominal raphe, and neural sheath in the spinal cord. As yet another example, the surgical laser system 10 may be used to treat bones, cartilage, ligaments, and tendons. As still another example, the surgical laser system 10 may be used to treat the brain, such as dura matter of the brain. As another example, the surgical laser system 10 may be used to treat lymph node CT or spleen CT. As another example, the surgical laser system 10 may be used to treat vascular vessels and the heart. As a further example, the surgical laser system 10 may be used to treat muscles.

The surgical laser system 10 includes a laser 12 coupled to one end of a connector assembly 14. An opposite end of the connector assembly 14 is connected to a hand-piece 16 having a tip 18. The connector assembly 14 delivers laser energy from the laser 12 to the hand-piece 16. The connector assembly 14 may be any desired assembly that delivers laser energy from the laser 12 to the hand-piece 16, such as a fiber optic assembly, a collimated arm system, or an atomozied particle beam.

The laser 12 may be any desired laser. For example, the laser 12 may be an Er:YAG laser having a wavelength of about 2.94 μm. The laser 12 may also be a free electron laser (FEL). The laser 12 may be any desired diode-pumped solid state laser, an infrared laser, an ultraviolet laser, or a semiconductor diode laser, an electromagnetic gas laser, or a femtosecond laser.

The hand-piece 16 may include a laser head, such as an Er:YAG laser head, that is pumped by the laser 12 to generate and deliver laser radiation through the tip 18. It is contemplated that the hand-piece 16 may be remotely connected with the laser 12. The tip 18 may be a contact tip or a non-contact tip. It is contemplated that the tip 18 may be made of any desired material, such as quartz, sapphire, or any other rare or basic earth elements.

The system 10 may also include a 2D or 3D scanning laser (not shown) for moving the laser radiation produced by the laser 12 in a desired pattern over the tissue. The system 10 may also incorporate a display, such as a holographic display or an LCD display. The system 10 may also incorporate robotic devices and/or components (not shown) for producing or controlling the radiation produced by the laser 12 or other device (not shown) in a desired pattern over the tissue. The system 10 may further incorporate operation via local or remote device. It is contemplated that the laser system 10 may include a scanning mechanism having a slit lamp and a gonioscope with or without the tip 18.

The system 10 may be used to remove any desired connective tissue by ablating the tissue. The desired connective tissue may be ablated to form perforations or pores in the connective tissue. Normal tissue healing is at least partially affected to maintain the perforations or pores in the connective tissue. By this, it is meant that the system 10 inhibits, disrupts, restricts, or otherwise causes the tissue to deviate from healing, repairing, or regenerating in a manner conforming to the usual or ordinary course of nature, producing observable deficiencies therein.

The fundamental and biomechanical properties of the connective tissue may be improved by formation of the perforations. The formation of perforations interacts with and affects the fundamental mechanisms involved in the immunology, biochemistry and molecular genetics of connective tissue metabolism. Furthermore, tension or contracture in the connective tissue may be reduced. The connective tissue may be ablated to at least 90% of the depth or thickness of the connective tissue.

The system 10 may ablate, excise, incise, vaporize, or puncture the tissue. This may be done along any axis, such as a transverse axis, sagital axis, frontal axis, or coronal axis with a single or plural repetitions (e.g., single or multiple ablations, excisions, incisions, vaporizations, or punctures). Alternatively, tension or contracture may be reduced by a shaving technique, with single or plural repetitions (e.g., single or multiple shavings) using various tips, to remove contiguous layers of tissue in desired areas. It is contemplated that the perforations may extend entirely through the depth or thickness of the tissue. If the perforations extend through the entire depth or thickness of the tissue, the perforated connective tissue may act as a flexible diaphragm pump.

Figure 2:
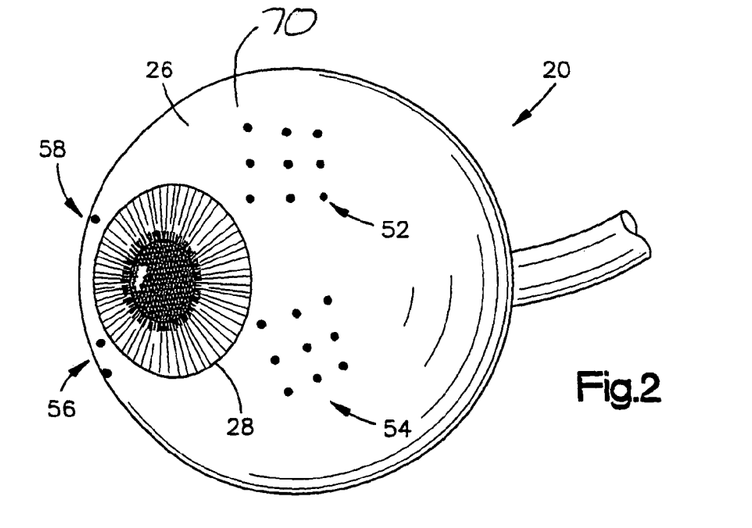
FIG. 2 is a schematic pictorial view of an eye showing perforation patterns formed in connective tissue of the eye.
Figure 3:
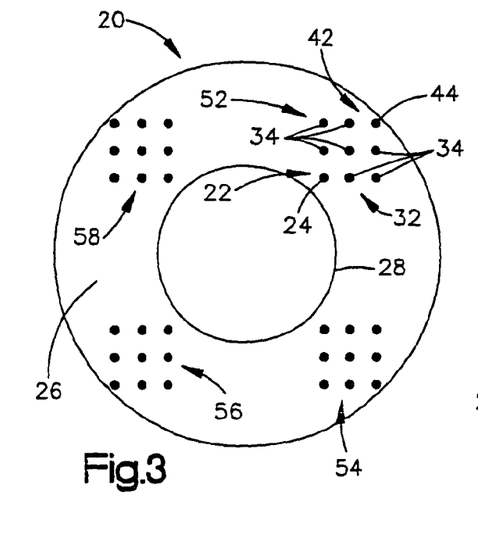
FIG. 3 is a schematic plan view of the eye of FIG. 2 showing the perforation patterns formed in the connective tissue of the eye.

The system 10 may be used to ablate or remove connective tissue, such as scleral tissue, of an eye 20 (FIGS. 2 and 3). A first desired pattern or matrix 22 of pores or perforations 24 is formed in the scleral tissue 26 of the eye 20. The first pattern 22 of perforations 24 is formed at a first distance from the outer diameter of the posterior surgical limbus 28 of the eye 20. The first distance is less than or equal to 1 mm from the outer diameter of the posterior surgical limbus of the eye 20. The first pattern or matrix 22 of perforations 24 may have any desired number of perforations 24.

As shown in the embodiment of FIGS. 2 and 3, the first pattern or matrix 22 of pores or perforations 24 may be a single, generally circular shaped pattern. It is contemplated that the first pattern 22 may have any desired shape. For example, the first pattern 22 may have a plurality of perforations 24 that form a cross-shaped pattern, a Z-shaped pattern, a U-shaped pattern, a V-shaped pattern, or an E-shaped pattern. It is also contemplated that the first pattern 22 may have perforations that form an oval, triangular, diamond, or rectangular shaped pattern or matrix.

A second pattern or matrix 32 of pores or perforations 34 is formed in the scleral tissue 26 of the eye 20. The second pattern 32 of perforations 34 is formed at a second distance from the outer diameter of the posterior surgical limbus 28 of the eye 20. The second distance is greater than or equal to 1 mm and less than or equal to 4.5 mm from the outer diameter of the posterior surgical limbus of the eye 20. The second pattern 32 of perforations 34 may have any desired number of perforations 34.

As shown in the embodiment of FIGS. 2 and 3, the second pattern or matrix 32 of pores or perforations 34 include a plurality of generally circular patterns. The second pattern 32 includes seven such perforations 34 arranged in three parallel rows. The outer rows of perforations 34 include two perforations each and the middle row of perforations includes three perforations. As shown in FIGS. 2 and 3, the perforations 34 of the middle row are offset from the perforations of the outer rows. It is contemplated that the second pattern or matrix 32 may have any desired shape. For example, the second pattern 32 may have a plurality of perforations 34 that form a cross-shaped pattern, a Z-shaped pattern, a U-shaped pattern, a V-shaped pattern, or an E-shaped pattern. It is also contemplated that the second pattern 32 may have perforations that form an oval, triangular, diamond, or rectangular shaped pattern or matrix.

A third pattern or matrix 42 of pores or perforations 44 is formed in the scleral tissue 26 of the eye 20. The third pattern or matrix 42 is substantially similar to the first and second patterns 22 and 32. The third pattern 42 of perforations 44 is formed at a third distance from the outer diameter of the posterior surgical limbus 28 of the eye 20. The third distance is greater than or equal to 4.5 mm from the outer diameter of the posterior surgical limbus of the eye 20. The third pattern or matrix 42 of perforations 44 may have any desired number of perforations 44.

As shown in the embodiment of FIGS. 2 and 3, the third pattern or matrix 42 of pores or perforations 44 may be a single circular shaped shaped pattern. It is contemplated that the third pattern 42 may have any desired shape. For example, the third pattern 42 may have a plurality of perforations 44 that form a cross-shaped pattern, a Z-shaped pattern, a U-shaped pattern, a V-shaped pattern, or an E-shaped pattern. It is also contemplated that the third pattern 42 may have perforations that form an oval, triangular, diamond, or rectangular shaped pattern.

The first, second, and third patterns or matrices 22, 32, and 42 may have the same shape of have different shapes. The first, second, and third patterns 22, 32, and 42 (FIG. 3) are formed along the same radial line extending from the outer diameter of the posterior surgical limbus 28 of the eye 20.

The first, second and third patterns or matrices 22, 32, and 42 define a first set 52 of patterns or matrices. The first set 52 of patterns or matrices is formed in a first quadrant of the eye 20. Second, third and fourth sets 54, 56, and 58 of patterns or matrices are formed in second, third, and fourth quadrants of the eye. The first, second, third, and fourth sets 52, 54, 56, and 58 of patterns may be identical. The four sets 52, 54, 56, and 58 of patterns each are arranged to have an overall diamond shape. It is contemplated that the first, second, third and fourth sets 54, 54, 56 and 58 may have a different number of patterns, differently shaped patterns, or a different number of perforations. It is contemplated that any desired number of sets of patterns of perforations may be formed in the scleral tissue 26 of the eye 20.

Figure 2A:
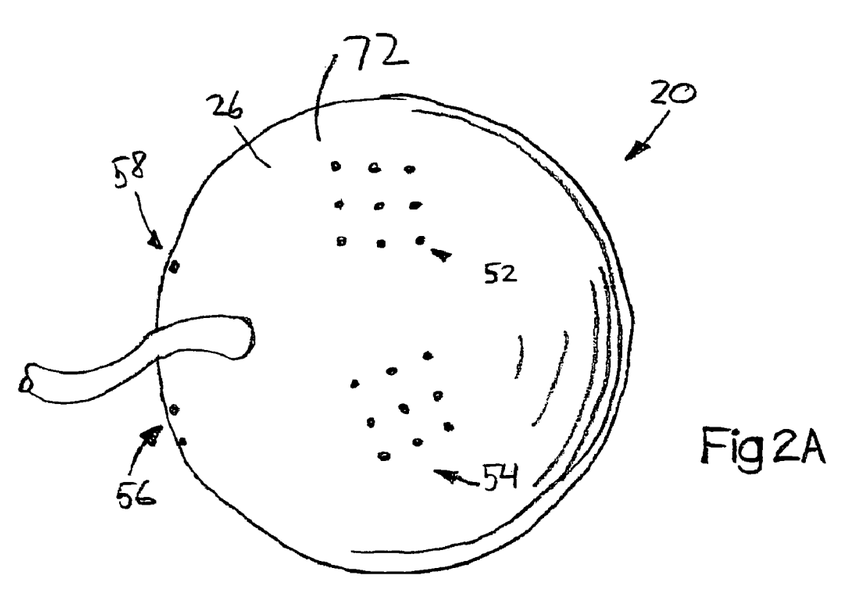
FIG. 2a is a schematic pictorial view of an eye showing perforation patterns formed in connective tissue of the eye.

In FIGS. 2 and 3, the first, second, third and fourth sets 54, 54, 56 and 58 are located on the anterior portion 70 of the eye 20. The sets 54, 54, 56 and 58 could, however, be located on the posterior of the eye 20. This is shown in FIG. 2A. As shown in FIG. 2A, the first, second, third and fourth sets 54, 54, 56 and 58 are arranged on the posterior 72 of the eye 20. As with the sets 54, 54, 56 and 58 on the anterior 70, the sets on the posterior 70 of the eye 20 may have a different number of patterns or matrices, differently shaped patterns, or a different number of perforations.

The pores or perforations 24, 34, and 44 may have any desired shape, such as cylindrical, pyramidal or tetrahedral. The perforations 24, 34, and 44 are formed to at least 90% of the depth or thickness of the scleral tissue 26. The perforations 24, 34, and 44 may be formed entirely through the scleral tissue 26 to the subchoroidal lamina so that the scleral tissue may act as a diaphragm pump. The perforations 24, 34, and 44 are formed by moving the hand-piece 16 or any surgical tool in a direction toward the tissue without moving in a direction extending along the surface of the tissue. The movement is repeated until the desired depth of the perforation is achieved. The perforations 24, 34, and 44 may improve uvealscleral aqueous flow to decrease the intraocular pressure of the eye 20.

The pores or perforations 24, 34, and 44 may have inner walls that are spaced from each other a distance that alters the fundamental mechanisms involved in the immunology, biochemistry and molecular genetics of connective tissue metabolism in such a way as to inhibit normal tissue healing, repair, or regeneration to prevent total healing of the perforations 24, 34, and 44 in the connective tissue. The inner walls of the perforations 24, 34, and 44 may be spaced from each other by a distance greater than 400 µm. It is also contemplated that the inner walls of the perforations 24, 34, and 44 may be spaced from each other by a distance greater than 600 µm.

The perforations may be filled with a scarring inhibitor substance such as a porous collagen-glycosaminoglican scaffold. An example of such a porous collagen-glycosaminoglican scaffold is made by Mediking under the tradename OcculusGen. Alternatively, the perforations may be filled with a biological glycoprotein or a synthetic glycoprotein. As another alternative, the perforations may be filled via the application of a biologically compatible product, which can be in the form of a liquid, a gel, or a porous solid. The perforations may also be treated with a sealant. An examples of such a sealant is made by Johnson and Johnson under the tradename Band-Aid® brand liquid bandage; and a similar product is made by Spenco under the tradename $2^{nd}$ Skin®. As a further alternative, the perforations may be filled via application or treatment to facilitate an ionic reaction, chemical reaction, photonic reaction, organic reaction, inorganic reaction, electronic reaction, or a combination of these reactions to disrupt normal tissue healing.

Although the pores or perforations in the connective tissue have been described as being formed by ablating the tissue using laser energy, it is contemplated that the perforations could be formed using any desired surgical tool, such as a diamond knife, ruby knife, or a radio frequency device.

Figure 4:
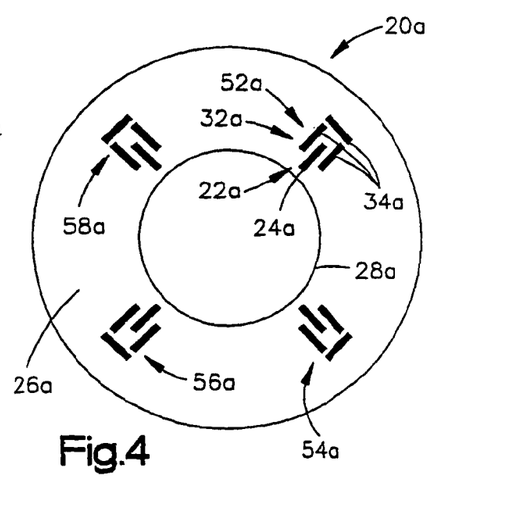
FIG. 4 is a schematic plan view of the eye of FIG. 2 showing alternative perforation patterns formed in the connective tissue of the eye.

An example of an alternative perforation patterns is illustrated in the embodiment shown in FIG. 4. The embodiment of FIG. 4 is similar to the embodiment of FIGS. 1 and 2.

Therefore, in FIG. 4, similar reference numbers are used, with the suffix "a" being used in FIG. 4 for clarity.

As shown in FIG. 4, the first pattern or matrix 22a includes perforations 24a that are arranged in a generally rectangular configuration. The first pattern 22a extends generally radially from the from the outer diameter of the posterior surgical limbus 28a of the eye 20a. The second pattern or matrix 32a includes three perforations 34a, each of which are arranged in a generally rectangular configuration. Two of the perforations 34a are positioned on opposite sides of the first pattern 22a, extend parallel to the first pattern, and are offset longitudinally from the first pattern. A third perforation 34a of the second pattern 32a extends transverse (perpendicular) to the remaining two perforations and is positioned, and is positioned adjacent ends of the perforations of the other two perforations of the second pattern distal to the outer diameter of the posterior surgical limbus 28a of the eye 20a.

The first and second patterns or matrices 22a and 32a define a first set 52a of patterns or matrices. The first set 52a of patterns is formed in a first quadrant of the eye 20a. Second, third and fourth sets 54a, 56a, and 58a of patterns or matrices are formed in second, third, and fourth quadrants of the eye 20a. The first, second, third, and fourth sets 52a, 54a, 56a, and 58a of patterns may be identical. The four sets 52a, 54a, 56a, and 58a may have a different number of patterns, differently shaped patterns, or a different number of perforations. It is contemplated that any desired number of sets of patterns of perforations may be formed in the scleral tissue 26a of the eye 20a. Like the embodiment of FIGS. 2-3, the four sets 52a, 54a, 56a, and 58a of FIG. 4 may be located on the anterior of the eye (shown), the posterior of the eye (not shown), or both.

From the above, it will be appreciated that the present invention relates to a system for treating connective tissue. The system include means for forming perforations in the connective tissue to at least 90% of the depth of the connective tissue. The system also includes means for at least partially affecting normal healing of the perforations.

It will also be appreciated that the present invention relates to a system for treating connective tissue to increase elasticity of the tissue comprising. The system includes means for removing connective tissue of an eye to form a first desired pattern of perforations in the connective tissue of the eye at a first distance from the outer diameter of the posterior surgical limbus of the eye, the first desired pattern of perforations having a plurality of perforations. The system also includes means for removing tissue from the eye to form a second desired pattern of perforations in the tissue of the eye at a second distance from the outer diameter of the posterior surgical limbus of the eye, the second desired pattern of perforations having a plurality of perforations.

It will be understood that the above description of the present invention is susceptible to various modifications, changes and adaptations, and the same are intended to be comprehended within the meaning and range of equivalents of the appended claims. The presently disclosed embodiments are considered in all respects to be illustrative, and not restrictive. The scope of the invention is indicated by the appended claims, rather than the foregoing description, and all changes that come within the meaning and range of equivalence thereof are intended to be embraced therein.

The invention claimed is:

1. A method of affecting the biomechanical properties of an eye having scleral tissue, having a surface, the method comprising:

forming a first closely arranged, two-dimensional array of pores on the surface of the scleral tissue, wherein the two-dimensional array of pores has an outline that forms a polygonal shape on the surface of the scleral tissue; wherein the pores have inner walls that are spaced a distance from each another; and at least partially affecting normal healing of the pores.

2. The method of claim 1 including filling the pores with a substance that at least partially affects normal healing of the pores.

3. The method of claim 1 including filling the pores with a porous collagen-based scaffold.

4. The method of claim 1 including filling the pores with a sealant.

5. The method of claim 1, wherein the eye has a posterior surgical limbus having an outer diameter and wherein the two-dimensional array of pores is formed at a first distance that is less than or equal to 1 mm from the outer diameter of the posterior surgical limbus of the eye.

6. The method as set forth in claim 5, further comprising forming a second closely arranged, two dimensional array of pores on the surface of the scleral tissue at a second distance that is greater than or equal to 1 mm and less than or equal to 4.5 mm from the outer diameter of the posterior surgical limbus of the eye.

7. The method as set forth in claim 5 further comprising forming a third closely arranged, two dimensional array of pores on the surface of the scleral tissue at a third distance from the outer diameter of the posterior surgical limbus of the eye.

8. The method as set forth in claim 7 wherein the third distance is greater than or equal to 4.5 mm from the outer diameter of the posterior surgical limbus of the eye.

9. The method as set forth in claim 7 including forming the first, second and third closely arranged, two-dimensional array of pores in a radial line extending from the corneal center of the eye.

10. The method of claim 1, wherein the first closely arranged, two-dimensional array of pores forms at least one of the following: a rectangular matrix, a square matrix, a diamond matrix, or a central hexagonal matrix.

11. The method of claim 1, wherein the first closely arranged, two-dimensional array of pores is located on the posterior portion of the eye.

12. The method of claim 1, wherein each pore has inner walls, and wherein the inner walls are spaced from each other by a distance greater than 400 μm.

13. The method of claim 1, wherein the distance is greater than 400 microns.

14. The method of claim 1, wherein the distance is greater than 600 microns.

15. A method of using a laser system, having a laser, to treat an eye having scleral tissue, having a thickness and a surface, the method comprising:

using the laser to form a plurality of generally quadrilateral shaped matrices of pores, each matrix having a central hexagon, on the surface of the scleral tissue;

wherein the pores have inner walls that are spaced a distance from each another; and filling each pore with a collagen-based scaffold.

* * * * *

US007871404C1

(12) INTER PARTES REEXAMINATION CERTIFICATE (696th)
United States Patent
Hipsley (10) Number: US 7,871,404 C1
(45) Certificate Issued: Sep. 18, 2013

(54) SYSTEM AND METHOD FOR TREATING CONNECTIVE TISSUE

(75) Inventor: Annmarie Hipsley, Silver Lake, OH (US)

(73) Assignee: Ace Vision Euro, Ltd, Manchester (GB)

Reexamination Request:
No. 95/000,644, Sep. 15, 2011

Reexamination Certificate for:
Patent No.: 7,871,404
Issued: Jan. 18, 2011
Appl. No.: 11/376,969
Filed: Mar. 15, 2006

Related U.S. Application Data

(60) Provisional application No. 60/662,026, filed on Mar. 15, 2005.

(51) Int. Cl.
*A61B 18/20* (2006.01)
(52) U.S. Cl.
USPC ................................. 606/5; 604/4; 128/898
(58) Field of Classification Search
None
See application file for complete search history.

(56) References Cited

To view the complete listing of prior art documents cited during the proceeding for Reexamination Control Number 95/000,644, please refer to the USPTO's public Patent Application Information Retrieval (PAIR) system under the Display References tab.

*Primary Examiner* — Jeffrey R Jastrzab (57) ABSTRACT

A method and system of treating connective tissue to alter the biomechanical and fundamental properties of the connective tissue by forming perforations in the connective tissue to at least 90% of the depth or thickness of the connective tissue and maintaining the perforations in the connective tissue. The method alters the tissue to enhance the fundamental mechanisms involved in the immunology, biochemistry, and molecular genetics of the metabolism of the connective tissue. The connective tissue may be any desired connective tissue. The connective tissue of the eye may be removed to form a first desired pattern of perforations in the connective tissue of the eye at a first distance from the corneal center of the eye. Connective tissue is removed from the eye to form a second desired pattern of perforations in the tissue of the eye at a second distance from the corneal center of the eye.

INTER PARTES REEXAMINATION CERTIFICATE ISSUED UNDER 35 U.S.C. 316

THE PATENT IS HEREBY AMENDED AS INDICATED BELOW.

AS A RESULT OF REEXAMINATION, IT HAS BEEN DETERMINED THAT:

The patentability of claim 15 is confirmed.

Claims 1-14 are cancelled.

* * * * *

(12) EX PARTE REEXAMINATION CERTIFICATE (10547th)
United States Patent
Hipsley (10) Number: US 7,871,404 C2
(45) Certificate Issued: Mar. 20, 2015

(54) SYSTEM AND METHOD FOR TREATING CONNECTIVE TISSUE

(75) Inventor: Annmarie Hipsley, Silver Lake, OH (US)

(73) Assignee: Ace Vision Euro Ltd, Manchester (GB)

Reexamination Request:
No. 90/013,100, Dec. 19, 2013

Reexamination Certificate for:
Patent No.: 7,871,404
Issued: Jan. 18, 2011
Appl. No.: 11/376,969
Filed: Mar. 15, 2006

Reexamination Certificate C1 7,871,404 issued Sep. 18, 2013

Related U.S. Application Data

(60) Provisional application No. 60/662,026, filed on Mar. 15, 2005.

(51) Int. Cl.
*A61B 18/20* (2006.01)
*A61F 9/008* (2006.01)

(52) U.S. Cl.
CPC .............. *A61F 9/008* (2013.01); *A61F 9/00808* (2013.01); *A61F 2009/00865* (2013.01); *A61F 9/00825* (2013.01); *A61F 9/00802* (2013.01); *A61F 9/00838* (2013.01)

USPC ..................................... 606/5; 606/4; 128/898

(58) Field of Classification Search
None
See application file for complete search history.

(56) References Cited

To view the complete listing of prior art documents cited during the proceeding for Reexamination Control Number 90/013,100, please refer to the USPTO's public Patent Application Information Retrieval (PAIR) system under the Display References tab.

*Primary Examiner* — Catherine S Williams (57) ABSTRACT

A method and system of treating connective tissue to alter the biomechanical and fundamental properties of the connective tissue by forming perforations in the connective tissue to at least 90% of the depth or thickness of the connective tissue and maintaining the perforations in the connective tissue. The method alters the tissue to enhance the fundamental mechanisms involved in the immunology, biochemistry, and molecular genetics of the metabolism of the connective tissue. The connective tissue may be any desired connective tissue. The connective tissue of the eye may be removed to form a first desired pattern of perforations in the connective tissue of the eye at a first distance from the corneal center of the eye. Connective tissue is removed from the eye to form a second desired pattern of perforations in the tissue of the eye at a second distance from the corneal center of the eye.

EX PARTE REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claim 15 is confirmed.

Claims 1-14 were previously cancelled.

\* \* \* \* \*